United States Patent [19]
Leone-Bay et al.

[11] Patent Number: 4,730,046
[45] Date of Patent: Mar. 8, 1988

[54] PREPARATION OF ARYL HALIDES

[75] Inventors: Andrea Leone-Bay; Elliott Bay, both of Ridgefield, Conn.; Peter E. Timony, Valley Cottage, N.Y.

[73] Assignee: Stauffer Chemical Company, Westport, Conn.

[21] Appl. No.: 851,625

[22] Filed: Apr. 14, 1986

[51] Int. Cl.[4] .................. C07C 17/22; C07C 41/22; C07D 213/61; C07D 239/30
[52] U.S. Cl. ........................... 544/334; 546/345; 568/656; 570/141; 570/201
[58] Field of Search ............... 570/141, 201; 568/656; 546/345; 544/334

[56] References Cited

PUBLICATIONS

Limokhin et al., Chemical Abstracts, vol. 101, (1984).
Matyushecheva et al., Chemical Abstracts, vol. 80, (1974).
Yagupol'skii et al., Chemical Abstracts, vol. 84, (1976).

*Primary Examiner*—Richard L. Raymond
*Attorney, Agent, or Firm*—Hensley M. Flash; Edwin H. Baker

[57] ABSTRACT

A process for selectively substituting an aromatic nitro group with a halo group which comprises contacting the nitroaromatic compound with a phosphorushalide of formula: $R_nPX_{5-n}$ wherein n is selected from 0, 1, 2 and 3; R is selected from the group consisting of C-6 to C-10 aryl and substituted aryl wherein the substituents are selected from the group consisting of: straight and branched chain alkyl, alkoxy, and haloalkyl; halogen, sulfonate and mixtures thereof; and X is a halogen in the presence of an arylphosphorusoxydihalide solvent. The use of an arylphosphorustetrahalide and particularly phenylphosphorustetrachloride is preferred. The arylphosphorustetrahalide can be prepared in situ by contacting a solution of the corresponding arylphosphorusdihalide in an arylphosphorusoxydihalide solvent with a halogen. The process can further comprise the step of heating the reaction mixture to maintain a temperature of from about 100° C. to about 175° C. for from about 1 hour to about 24 hours.

11 Claims, No Drawings

PREPARATION OF ARYL HALIDES

BACKGROUND OF THE INVENTION

1. Field of the Invention

This invention relates to a process for preparing aryl halides and in particular to a process for selectively substituting an aromatic nitro group with a halogen.

2. Related Information

A common problem facing organic chemists is the regio-specific halogenation of aromatic rings. One practical solution to this problem is the substitution of aromatic nitro groups by a halogen, e.g., chlorine. The Sandmeyer reaction is normally used to accomplish this conversion. The nitro group is reduced to an amine, diazotized, then reacted with copper chloride to give the corresponding chloroaromatic. A number of variations on this basic reaction are also known. Other methods of replacing an aromatic nitro group with a chlorine include irradiation in chloroform/hydrogen chloride solution, alkylative reduction by Grignard reactions quenched with sodium hypochlorite and treatment with thionylchloride in the vapor phase.

The Sandmeyer reaction is normally the process of choice and even though this synthesis involves many steps, it offers several advantages over direct halogenation. First of all, fluorides and iodides which can seldom be prepared by direct halogenation, can be obtained from the diazonium salts. Second, where direct halogenation yields a mixture of ortho and para isomers, the ortho isomer, at least, is difficult to obtain pure. On the other hand, orthod and para isomers of the corresponding nitro compounds, from which the diazonium salts ultimately come, can often be separated by fractional distillation. For example, the boiling points of ortho- and para-bromotoluenes are only 3° C. apart (82° C. and 85° C.). The boiling points of the corresponding ortho- and para-nitrotoluenes, however, are 16° C. apart (222° C. and 238° C., respectively).

The use of phosphorushalides of formula: $R_nPX_{5-n}$ wherein n is selected from 0, 1, 2 and 3; R is selected (when n is other than 0) from the group consisting of C-6 to C-10 aryl and substituted aryl wherein the substituents are selected from the group consisting of: straight and branched chain alkyl, alkoxy, and haloalkyl; halogen, sulfonate and mixtures thereof; and X is a halogen, and particularly the use of phenylphosphorustetrachloride (PPTC), as a reagent for organic synthesis is practically unknown when they contain aryl or substituted aryl groups. Timokhin, B. V.; Dmitriev, V. K., Dmitriev, V. I., *Zh. Obshch. Khim.* 1984, 54, 1290, reported the reaction of cyclohexene with PPTC to give trans-1,2-dichlorocyclohexane and 3-chlorocyclohexene. Mitrasov, Y. N.; Vladyko, E. D.; Kormachev, V. V. USSR SU Nos. 1,051,097 and 1,051,096 found that treatment of aliphatic aldehydes and ketones with PPTC produced geminal dichlorides. PPTC has also been used to produce tetrazines from hydrazines, see Yagupol'skii, L. M.; Matyushecheva, G. I.; Mikhailov, V. S.; Bulygina, L. A. USSR SU No. 498,300 and Matyushecheva, G. I.; Mikhailov, V. S. Yagupol'skii, L. M., *Zh. Org. Khim.* 1974, 10, 124.

SUMMARY OF THE INVENTION

An object of this invention is to provide a process for simply preparing arylhalides by selectively substituting the corresponding aromatic nitro group with a halo group.

A further object of this invention is the use of a phosphorushalide, and particularly an arylphosphorushalide such as PPTC, as a reagent in organic synthesis and particularly its use as a selective halogenating agent in the preparation of aryl halides.

Other objects and advantages of the present invention are described elsewhere within this specification.

This invention is a process for selectively substituting an aromatic nitro group with a halogen which comprises contacting a compound containing an aromatic nitro group with a phosphorushalide of formula: $R_nPX_{5-n}$ wherein n is selected from 0, 1, 2 and 3; R is selected from the group consisting of C-6 to C-10 aryl and substituted aryl wherein the substituents are selected from the group consisting of: straight and branched chain alkyl, alkoxy, and haloalkyl; halogen, sulfonate and mixtures thereof; and X is a halogen, in the presence of an arylphosphorusoxydihalide solvent and in an amount effective to selectively denitrohalogenate said compound. In this process, a preferred phosphurshalide, e.g., an arylphosphorustetrahalide, can be prepared in situ by contacting a solution of an arylphosphorusdihalide in an arylphosphorusoxydihalide solvent with a halogen. In preferred embodiments, the nitroaromatic compound is added to a solution containing the arylphosphorushalide and the resulting reaction mixture is heating to maintain a temperature of from about 100° C. to about 175° C. for from about 1 hour to about 24 hours. Phenylphosphorustetrahalide is a preferred arylphosphorustetrahalide and particularly the chloride and fluoride which are used to prepare the the corresponding chloro and fluoro benzene product.

DETAILED DESCRIPTION OF THE INVENTION

In the process of this invention, aromatic nitro groups are removed and replaced with halo groups. The major product resulting, has the aromatic nitro group replaced by a halo compound, i.e., after the nitro group is removed, thus this process is one for selectively substituting an aromatic nitro group with a halogen.

The compound containing the aromatic nitro group can be selected from the group consisting of C-6 to C-14 nitro aryl, substituted nitro aryls, five and six-membered heterocylic rings having 1 to 2 hetero-atom(s) selected from nitrogen and sulfur and having a nitro substituent as well as other optional substituents on the ring. The substituents on both the substituted nitro aryl and the heterocyclic rings can be selected from the group consisting of: straight and branched chain, C-1 to C-8 alkyls, C-1 to C-6 alkoxy, and C-1 to C-8 haloalkyls; sulfonates, halogens and mixtures thereof. A preferred haloalkyl substituent is trifluoromethyl. In fact, as long as at least one -NO₂ group is on the ring, the presence of other substituents should not interfere or at least not seriously interfere with the selective substitution reaction. Illustrative compounds containing the aromatic nitro group include substituted benzenes, pyrimidines, pyridines, and anthracenes.

The phosphorushalide useful in this invention is of the formula:

$$R_nPX_{5-n}$$

wherein n, R and X are defined above. A preferred compound is an arylphosphorus halide such as an arylphosphorustetrahalide and particularly an arylphosphorustetrahalide prepared in situ by contacting a solution of an arylphosphorusdihalide in an arylphosphorusoxydihalide solvent with a halogen. Another preferred phosphorushalide is when n=0, e.g., phosphorus pentahalide, particularly the pentachloride.

The aryl portion of arylphosphorustetrahalide, arylphosphorusdihalide, and arylphosphorusoxydihalide (if present) can be C-6 to C-10 aryl and substituted aryl wherein the substituents can be selected from the group consisting of: straight and branched chain alkyl, alkoxy, and haloalkyl; halogen, sulfonate and mixtures thereof. The halide portions of these compounds can be any of the halogens, e.g., chlorine, bromine, iodine, and fluorine, with chlorine and fluorine being preferred.

In this process, the aromatic nitro group is contacted with, for example, the preferred arylphosphorustetrahalide in the presence of an arylphosphorusoxydihalide solvent and in an amount effective to selectively denitrohalogenate said aromatic nitro group. The phosphorushalide can be prepared by any known method, and the preferred arylphosphorustetrahalide can preferably be prepared in situ by contacting a solution of an arylphosphorusdihalide in the solvent, arylphosphorusoxydihalide, with a halogen. In this preferred procedure, it is preferred to use the particular aryl halide and halogen group throughout the preparation, e.g., in the preparation of phenylphosphorustetrachloride, phenylphosphorusdichloride in a solution of phenylphosphorusoxydichloride is contacted with chlorine gas. It is also preferred that the compound containing the aromatic nitro group be added to the solution containing the arylphosphorushalide.

It is believed that the mere contacting of the compound containing the aromatic nitro group and the phosphorushalide in the presence of an arylphosphorusoxydihalide solvent can result in the preparation of certain quantities of the denitrohalogenated compound. However, heating the reaction mixture over a period of time can result in increased yields. The reaction mixture can be heated to maintain a temperature of from about 100° C. to about 175° C. for from about 1 hour to about 24 hours and a temperature range of from about 145° C. to about 160° C. maintained for about 5 hours is particularly preferred. The reactants utilized in the process of the present invention are generally employed in stoichiometric amounts, although an excess of any reagent can be used, if desired. The quantity of undesired side products, however, can be minimized by the use of approximately stoichiometric amounts of reactants. No catalyst is used or is necessary in the processes of the present invention.

The reaction times can vary over relatively wide ranges and can easily be determined by one of ordinary skill in the art. Factors affecting reaction time can include the choice of a specific reactant and a specific temperature. Increases in temperature and reactant concentrations up to stoichiometric amounts can result in decreased reaction times. Dilute reactants usually require longer reaction time than the more concentrated reactions. The reaction is run at atmospheric pressure and it is believed that increased pressure can increase the reaction rate.

The following generalized equation represents the process of this invention:

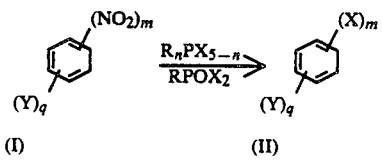

$R_nPX_{5-n}$ is the phosphorushalide and $RPOX_2$ is the arylphosphorusoxydihalide solvent which are both described above. Formula (I) represents the nitroaromatic compound, here depicted as a nitrophenyl compound. M is $\geq 1$ and $\leq 6$ for the nitrophenyl compound i.e. there must be at least one nitro group and can be up to the maximum allowable six nitro groups. Y represents the optional substituents on the ring and q, the number of substituents, can be 0, 1, 2, 3, 4 or 5. Formula (II) represents the resulting halogenated product in which each nitro group is replaced by the halogen X.

The following experiments describe various embodiments of this invention. Other embodiments will be apparent to one of ordinary skill in the art from a consideration of this specification or practice of the invention disclosed herein. It is intended that the specification and experiments be considered as exemplary only, with the true scope and spirit of the invention being indicated by the claims which follow the experiments.

EXPERIMENTS

The following experiments demonstrate the use of phenylphosphorustetrachloride (PPTC) in benzenephosphorusoxydichloride (BPOD) at 170° C. to convert nitro- aromatics to chloroaromatics.

The conversion of 1,2-dichloro-3-nitrobenzene to 1,2,3-trichlorobenzene is typical.

Chlorine gas (400 mg, 573 millimoles) was bubbled into a solution of benzenephosphorusdichloride (789 microliters, 573 millimoles) in BPOD (10 ml) at room temperature. The initially clear colorless solution became warm and turned pale yellow, but remained clear. To this mixture was added 1,2-dichloro-3-nitrobenzene (1.0 g, 573 millimoles) and then the reaction mixture was heated to 170° C. for 5 hours. The cooled reaction mixture was then poured onto crushed ice/water (100 ml) and neutralized with 50% aqueous sodium hydroxide. After extracting with ether, the ether extracts were dried and concentrated in vacuo to yield 1,2,3-trichlorobenzene (880 mg, 94 weight %).

Table I below summarizes the results obtained using PPTC in BPOD to prepare chloroaromatics from various nitroaromatics following the procedure described above.

TABLE 1
Chloroaromatics From Nitroaromatics Using PPTC in BPOD

| Starting Material | Product | Wt. % Yield |
| --- | --- | --- |
| 1,2-dichloro-3-nitrobenzene | 1,2,3-trichlorobenzene | 94 |
| 2-nitro-1-chloro-4-trifluoromethylbenzene | 1,2-dichloro-4-trifluoromethylbenzene | 67 |
| 2-chloro-1-nitrobenzene | 1,2-dichlorobenzene | 78 |
| 4-chloro-1-nitrobenzene | 1,4-dichlorobenzene | 73 |
| 4-chloro-1,2-dinitrobenzene | 1,2,4-trichlorobenzene | 86 |
| 2-nitroanisole | 2-chloroanisole | 66 |
| nitrobenzene | chlorobenzene | 93 |
| 2-chloro-3-nitropyridine | 2,3-dichloropyridine | 81 |
| 4,6-dichloro-5-nitropyrimidine | 4,5,6-trichloropyrimidine | 82 |
| 9-nitroanthracene | 9-chloroanthracene | 90 |

What is claimed is:

1. A process for selectively substituting an aromatic nitro group with a halogen which comprises contacting a compound containing an aromatic nitro group with a phosphorushalide of formula: $R_nPX_{5-n}$ wherein n is selected from 0, 1, 2 and 3; R is selected from the group consisting of C-6 to C-10 aryl and substituted aryl wherein the substituents are selected from the group consisting of: straight and branched chain alkyl, alkoxy, and haloalkyl; halogen, sulfonate and mixtures thereof; and X is a halogen, in the presence of an arylphosphorusoxydihalide solvent and in an amount effective to selectively denitrohalogenate said compound.

2. The process of claim 1 wherein the phosphorushalide is an arylphosphorustetrahalide prepared in situ by contacting a solution of an arylphosphorusdihalide in an arylphosphorusoxydihalide solvent with a halogen gas.

3. The process of claim 2 wherein the nitroaromatic compound is added to the solution containing the arylphosphorustetrahalide.

4. The process of claim 3 which further comprises the step of heating the mixture resulting from the addition of the nitroaromatic compound.

5. The process of claim 4 wherein the resulting mixture is heated to maintain a temperature of from about 100° C. to about 175° C. for from about 1 hour to about 24 hours.

6. The process of claim 5 wherein the arylphosphorustetrahalide is phenylphosphorustetrahalide.

7. The process of claim 6 wherein the phenylphosphorustetrahalide is prepared from phenylphosphorusdihalide in phenylphosphorusoxydihalide.

8. The process of claim 7 wherein the halides are chlorides and the halogen is chlorine.

9. The process of claim 7 wherein the halides are fluorides and the halogen is fluorine.

10. The process of claim 1 wherein the phosphorushalide is phosphorus pentachloride.

11. The process of claim 10 wherein the nitroaromatic compound is added to a solution of the phosphorus pentachloride and the resulting mixture heated to maintain a temperature of from about 100° C. to about 175° C. for from about 1 hour to about 24 hours.

* * * * *